(12) United States Patent
Anderson et al.

(10) Patent No.: US 11,141,545 B2
(45) Date of Patent: Oct. 12, 2021

(54) SPRAYER TECHNOLOGY

(71) Applicants: Mark L. Anderson, Hudson, WI (US);
John Harmon, Spring Valley, WI (US);
Brian Husby, Spring Valley, WI (US);
Kevin O'Connell, Omaha, NE (US)

(72) Inventors: Mark L. Anderson, Hudson, WI (US);
John Harmon, Spring Valley, WI (US);
Brian Husby, Spring Valley, WI (US);
Kevin O'Connell, Omaha, NE (US)

(73) Assignee: Mark L. Anderson, LLC, Spring Valley, WI (US)

( * ) Notice: Subject to any disclaimer, the term of this patent is extended or adjusted under 35 U.S.C. 154(b) by 718 days.

(21) Appl. No.: 15/530,096

(22) Filed: Dec. 1, 2016

(65) Prior Publication Data
US 2018/0154090 A1    Jun. 7, 2018

(51) Int. Cl.
*A61M 11/00*      (2006.01)
*A61M 15/08*      (2006.01)
(Continued)

(52) U.S. Cl.
CPC .......... *A61M 11/007* (2014.02); *A61M 15/08* (2013.01); *A61K 39/12* (2013.01);
(Continued)

(58) Field of Classification Search
CPC .. A61M 11/007; A61M 11/00; A61M 11/006; A61M 15/00; A61M 15/08;
(Continued)

(56) References Cited

U.S. PATENT DOCUMENTS 4,344,573 A * 8/1982 De Felice ............... B05B 11/02
                                                                                128/203.15
4,923,448 A * 5/1990 Ennis, III ................ A61M 5/31
                                                                                128/200.14
(Continued)

FOREIGN PATENT DOCUMENTS

WO      WO-03061839 A1 * 7/2003 ........... B05B 1/3436

OTHER PUBLICATIONS

Hajj Hussein I, Chams N, Chams S, et al. Vaccines Through Centuries: Major Cornerstones of Global Health. Front Public Health. 2015;3:269. Published Nov. 26, 2015. doi:10.3389/fpubh.2015.00269 (Year: 2015).*

(Continued)

*Primary Examiner* — Nilay J Shah
(74) *Attorney, Agent, or Firm* — Skinner and Associates; Joel D. Skinner, Jr.

(57) ABSTRACT

A spray apparatus adapted to be connected to a fluid supply such as a syringe to spray a predetermined pattern of spray fluid to a target area such as the tissues of an animal or human. The sprayer delivers a predetermined dose of a medicament, vaccine or the like to the nasal or other cavity of an animal or human patient. The sprayer includes a base member and a cap member which is connected to the base member. The base member is connectible to the fluid supply. Spray is discharged from the distal or outward end of the cap member. The base member has a central, longitudinal lumen having a predetermined configuration. Fluid traverses the lumen and is discharged through a central aperture of the cap, which also has a predetermined configuration. The cap central lumen and spray discharge aperture are aligned with the base lumen.

23 Claims, 8 Drawing Sheets

(51) Int. Cl.
*A61K 39/00* (2006.01)
*A61K 39/12* (2006.01)
*A61M 15/00* (2006.01)

(52) U.S. Cl.
CPC .. *A61K 2039/543* (2013.01); *A61K 2039/552* (2013.01); *A61M 15/0025* (2014.02); *A61M 2250/00* (2013.01); *C12N 2760/16034* (2013.01); *C12N 2760/16134* (2013.01)

(58) Field of Classification Search
CPC  A61M 15/0025; A61M 11/08; A61M 11/008; A61M 2210/0618; A61B 2017/00522; A61B 17/545; A61B 18/0218; A61B 2218/003
See application file for complete search history.

(56) References Cited

U.S. PATENT DOCUMENTS

| | | | |
|---|---|---|---|
| 6,427,682 B1* | 8/2002 | Klimowicz | A61M 11/005 128/200.14 |
| 2003/0017150 A1* | 1/2003 | Torphy | C07K 14/47 424/131.1 |
| 2006/0160759 A1* | 7/2006 | Chen | A61K 9/5146 514/44 A |
| 2008/0210227 A1* | 9/2008 | Godfrey | A61M 11/08 128/200.21 |
| 2011/0049265 A1* | 3/2011 | Vedrine | A61M 11/00 239/302 |
| 2012/0107414 A1* | 5/2012 | Lipp | A61K 9/0078 424/602 |
| 2016/0067144 A1* | 3/2016 | Chang | A61M 5/19 604/92 |

OTHER PUBLICATIONS

Patent translate: translation of WO 03/061839 A1 Aug. 15, 2019 of translation (Year: 2003).*

* cited by examiner

SPRAYER TECHNOLOGY

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to apparatus and methods of spraying fluids. More particularly, the invention relates to spraying apparatus and methods for use in veterinary medical and human medical applications. Most particularly, the invention relates to a spray atomizing apparatus adapted to be connected to a liquid supply such as a syringe, and methods of use and manufacture therefor. The techniques of the invention can also be used in other fields.

2. Background Information

Existing technology is believed to have significant limitations and shortcomings. For these and other reasons, a need exists for the present invention.

All US patents and patent applications, and all other published documents mentioned anywhere in this application are hereby incorporated by reference in their entirety.

BRIEF SUMMARY

The present invention provides a spray apparatus and method which are practical, effective, safe, and efficient, and which are believed to fulfill a need and to constitute an improvement over the background technology.

The invention provides a spray apparatus adapted to be connected to a fluid supply such as a syringe to spray a predetermined pattern of spray fluid to a target area such as the tissues of an animal or human. The sprayer is particularly well suited to delivering a predetermined dose of a liquid medicament, vaccine or the like to the nasal or other cavity of an animal or human patient. The sprayer includes a base member and a cap member which is connected to the base member. The base member is connectible to the fluid supply. Spray is discharged from the distal or outward end of the cap member. The base member has a central, longitudinal lumen having a predetermined configuration. Fluid traverses the lumen and is discharged through a central aperture of the cap, which also has a predetermined configuration. The cap central lumen and spray discharge aperture are aligned with the base lumen. Methods of use and manufacture are also disclosed.

In one aspect, the invention relates to a fluid sprayer adapted to connect to a fluid supply, comprising a base member having a first end and a second end, the base member having an outer wall defining a lumen open at the first end for communicative connection to the fluid supply, the lumen extending to the second end, the second end having at least one fluid egress aperture; and a cap member having a first end and a second end, the first end of the cap being connected to the second end of the base member, the cap member having an outer wall defining a lumen open at the first end and communicatively connected to the lumen of the base member through the at least one fluid egress aperture, the cap member further having a spray discharge aperture disposed at the second end, communicatively connected to the cap lumen.

In another aspect, the invention relates to a liquid sprayer adapted to connect to a fluid supply syringe for delivering medicaments and vaccines to animals and humans, comprising:

A. a tubular, cylindrical and elongated base member having a first end and a second end, the base member having an outer wall defining a lumen open at the first end for communicative connection to the fluid supply, the lumen extending to the second end, the second end having a plurality of fluid egress apertures separated by radial member, the base member lumen having a tapered first portion extending from the open first end, and a cylindrical second portion extending from the first portion to the fluid egress apertures, the base member further having a post member disposed at the second end of the base member extending outwardly, the post member having a predetermined length and diameter; and B. a tubular, cylindrical cap member having a first end and a second end, the first end of the cap being connected to the second end of the base member, the cap member having an outer wall defining a lumen open at the first end and communicatively connected to the lumen of the base member through the fluid egress apertures, the cap member further having a spray discharge aperture disposed at the second end, communicatively connected to the cap lumen, the cap member lumen further having a first portion for mating with the base member and at least two further portions communicatively connected to the fluid egress apertures of the base member for transmitting fluid from the base member to the spray discharge aperture, the at least two further lumen portions including a tapered portion communicatively connected to the base at least one fluid egress aperture, and a cylindrical portion extending from the tapered portion to the spray discharge aperture;

C. whereby the predetermined length and diameter of the base post are less than the length and diameter of the lumen of the cap member to thereby form a fluid transmission space communicatively connected to the spray discharge aperture.

Figure 5:
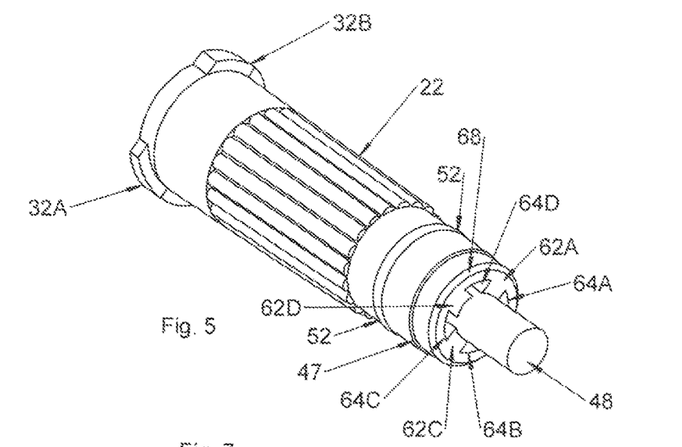
Figures 6, 8:
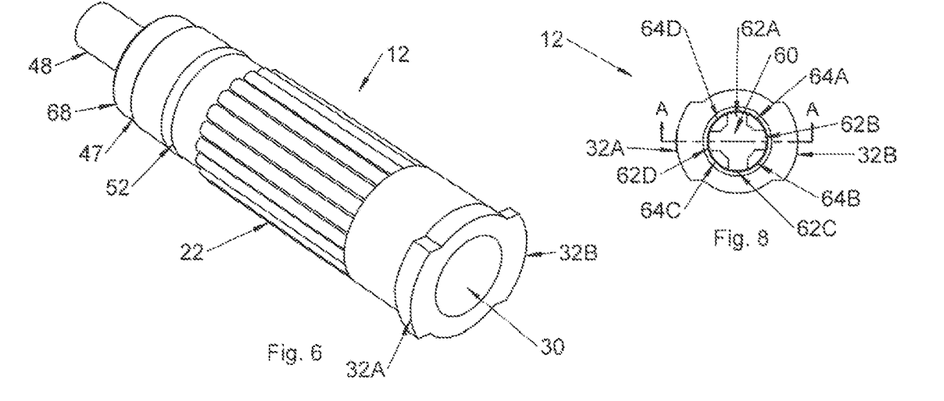
Figure 7:
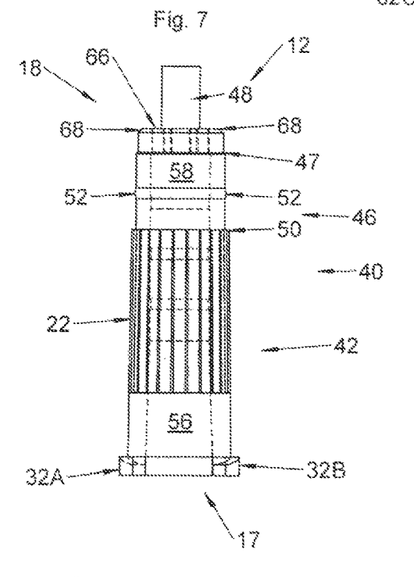
Figure 9:
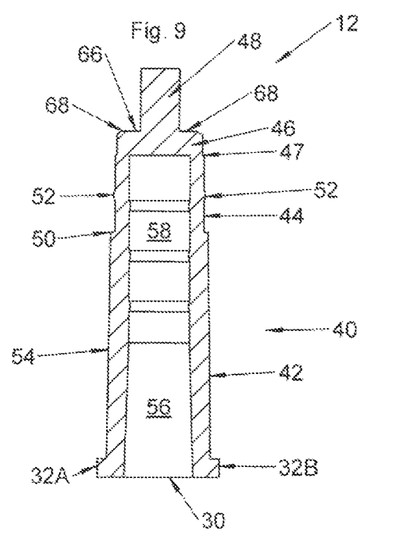
Figure 10:
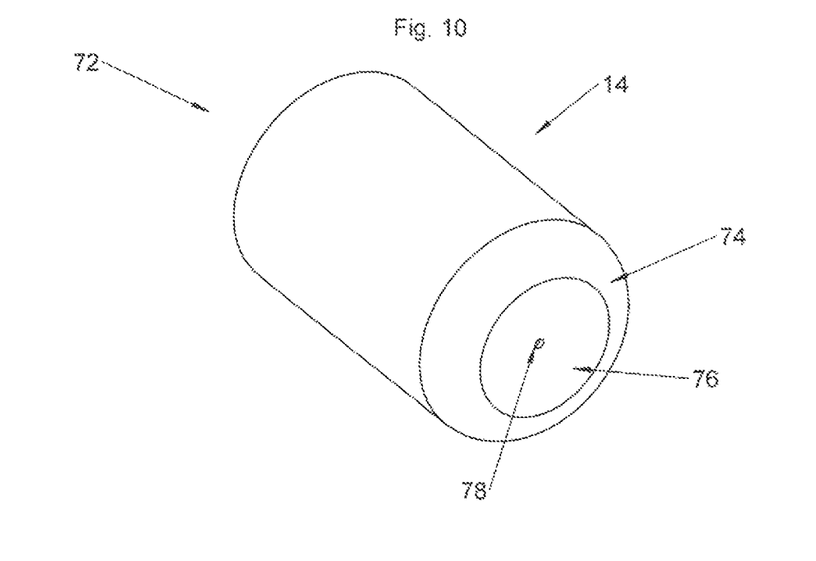
Figure 11:
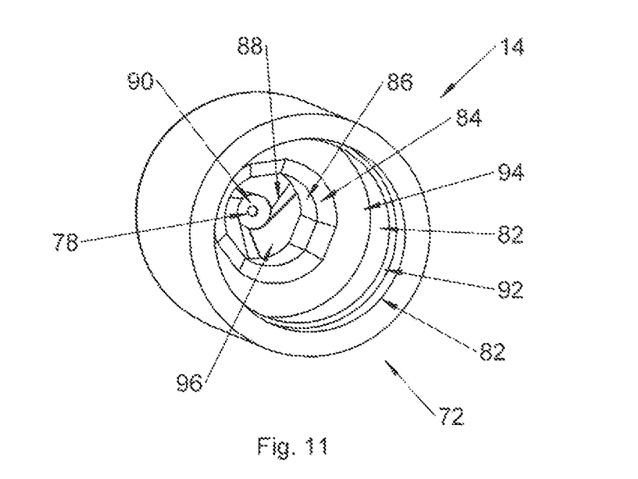
Figure 12:
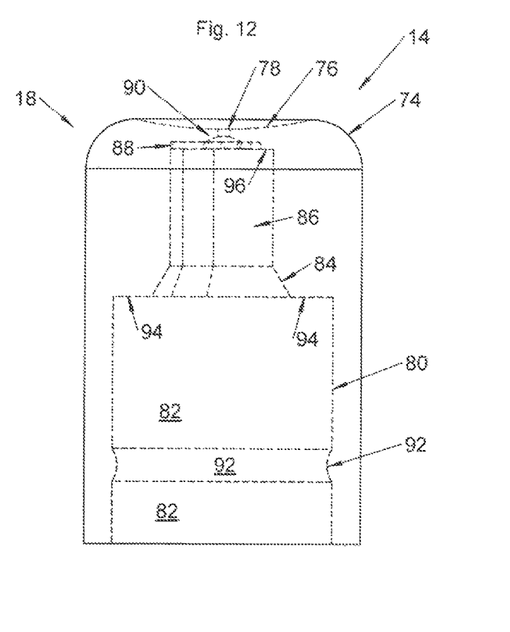
Figure 13A:
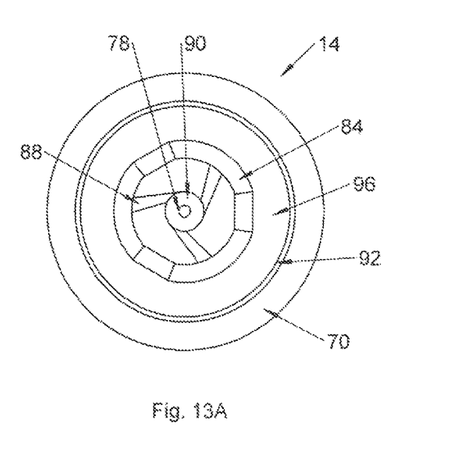
Figure 13B:
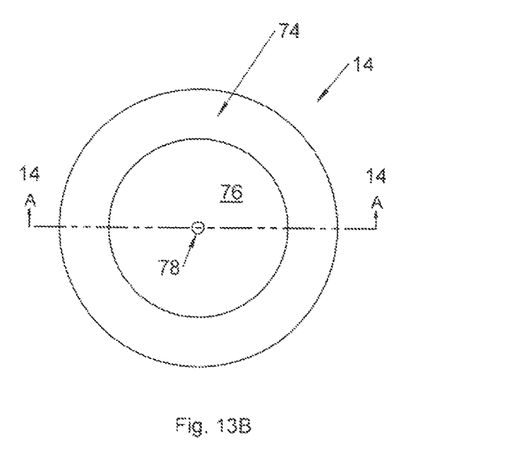
Figure 14:
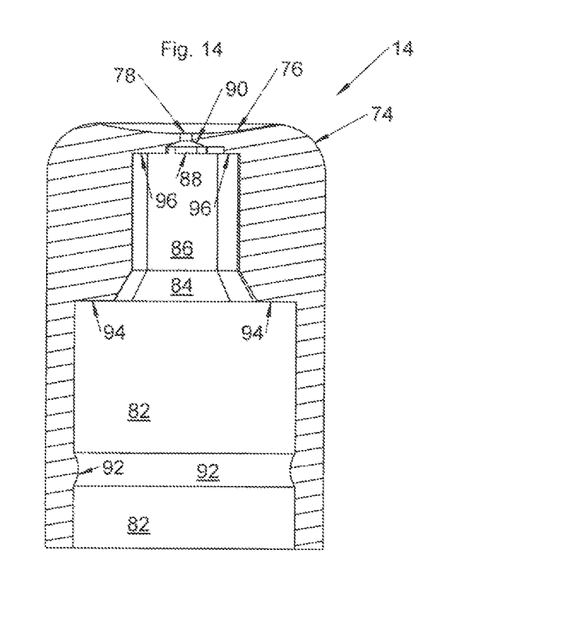

Other aspects of the invention provide a method of administering a liquid to an animal by intranasal atomization using the sprayer; a method to protect an animal against an infection caused by a microorganism comprising administering by intranasal atomization a vaccine comprising an antigen to upper respiratory tract of the animal by using the sprayer; a method of treating an infection in an animal caused by a microorganism comprising administering by intranasal atomization a liquid composition comprising a compound effective in treatment of the infection to the upper respiratory tract of the animal by using the sprayer; and a method of se of the device to administer a liquid to an animal by intranasal atomization.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

FIG. 1 is a perspective or isometric view of an embodiment of the spraying apparatus of the present invention.

FIG. 2 is a front view of the spraying apparatus.

FIG. 3 is a front view of the spraying apparatus, showing interior features thereof in phantom or cross hatched lines.

FIG. 4 is a longitudinal crossectional view of the spraying apparatus.

FIG. 5 is a perspective view of an embodiment of the body portion of the spraying apparatus, taken from the top or distal end thereof.

FIG. 6 is another perspective view of the body portion taken from the bottom thereof.

FIG. 7 is a front view of the body portion, partially in phantom showing interior features thereof.

FIG. 8 is a bottom view of the body portion.

FIG. 9 is a longitudinal crossectional view of the body portion.

FIG. 10 is a perspective view of an embodiment of the cap portion of the spraying apparatus, taken from the top or distal end thereof.

FIG. 11 is a further perspective view of the cap portion taken from the bottom thereof.

FIG. 12 is a front view of the cap portion, partially in phantom showing interior features thereof.

FIGS. 13 A and B are bottom and top views, respectively of the cap portion as shown in FIGS. 12 and 14.

FIG. 14 is a longitudinal crossectional view of the cap portion taken at line 14-14 of FIG. 13B.

FIG. 15 is a perspective view of the sprayer apparatus operatively connected to a liquid supply, namely a syringe.

DETAILED DESCRIPTION

1. Sprayer Apparatus; Methods of Construction, and General Methods of Use.

The spray apparatus or sprayer 10 of the present invention is useful for spraying fluids such as liquid medicaments, vaccines and the like on animal and human tissues. The device is particularly useful for atomizing and delivering liquid substances and compositions to tissues in the nasal cavity of animals and humans.

Referring to FIGS. 1, 2 and 15 one embodiment of the spray apparatus 10 adapted to be connected and disconnected to a fluid supply such as a syringe 20 or the like. The spray apparatus embodiment 10 shown has a generally tubular, cylindrical, elongated configuration. The sprayer 10 preferably has a grip area or pattern 22 disposed approximately at its midsection. The grip pattern 22 has longitudinally oriented columns and grooves. The columns preferably have a curvilinear configuration. Alternatively, the pattern may be knurled or other such surface. The first or proximal end 16 of the sprayer 10 is attachable to the distal or output end of the syringe 20. The proximal end 16 has an open or female type orifice 30 that mates with a complementary male type fitting of the fluid supply element or unit 20. The proximal end 16 further preferably has a flange arrangement for connection with a complementary mating arrangement of the fluid supply 20. In the embodiment shown, the flange arrangement consists of a pair of opposing flanges 32 A and B. The second or distal end 18 of the sprayer 10 extends outwardly away from the syringe 20. The distal end 18 is aimed at a target area such as nasal or other tissues of an animal or human patient and outputs a predetermined volume of fluid in an atomized spray having a predetermined effective spray pattern. The distal end 18 is insertable into an orifice or cavity of a patient, for example a nasal cavity. The sprayer 10 is easily disconnectible and removable from the fluid supply 20 to permit reuse of the fluid supply 20 with a clean, fresh sprayer 10 for use with the same or a different patient.

The particular embodiment of the sprayer 10 shown is used with an approximately 2.0 milliliters (ml.). syringe 20. The sprayer 10 has a length of approximately 1.045 inches (in.). The diameter of the distal end 18 is approximately 028 in. The inside diameter (ID) of the orifice 30 is approximately 0.17 in. and the outside diameter (OD) measure at the flanges 32 is approximately 0.30 in.

Referring also to FIGS. 3, 4, 5, 10 and 11, the sprayer 10 embodiment has a two-part structure including a base member 12 and a cap member 14. As is best shown in FIGS. 3 and 4, the proximal end of the cap member 14 is coupled to the distal end of the base member 12 in a tandem or in-line arrangement for operation. In the embodiment shown, the base member 12 has a preferred length of approximately 1.015 in. and the cap member 14 has a length of approximately 0.430 in. The base and cap member 12 and 14 are preferably constructed of a rigid polymeric material.

A preferred embodiment of the base member 12 is shown in detail in FIGS. 5-9. The base member 12 has a generally tubular, cylindrical, elongated configuration. It has a lateral wall 40 that extends distally from the orifice 30 and flanges 32. The wall 40 has a first portion 42, which includes the grip pattern columns and grooves, and a second portion 44 extends distally from the first portion and has a smooth, curvilinear exterior. The first portion 42 has a length which is slightly longer than the length of the second portion 44 and tapers inwardly distally. If functions primarily to mate with the syringe. Second portion 44 is cylindrical and does not taper. It reduces the residual volume of fluid throughput from the syringe or other fluid source. Exterior ledge 50 is formed at the intersection of the first and second portions 42 and 44, inset a predetermined distance with respect to first portion 42. A male, curvilinear snap connection ring 52 is disposed at approximately a midpoint of the second portion 44. It has predetermined length and thickness for mating with a complementary structure on the interior of the cap member 14 described below. Second portion 44 terminates at a terminal portion 46. The terminal portion 46 is inset slightly relative to the exterior of the second portion 44 thereby forming ledge 47 A post member 48 extends from the terminal portion 46. Post member 48 is cylindrical and has a predetermined diameter for mating with the cap as described further below. In the base 12 embodiment shown, the ID of the lumen portion 56 at the proximal end is preferably 0.170 in, and the ID at the transition between portion 56 and 58 is 0.150 in. This is also the diameter of the portion 58.

The base member 12 wall 40 and terminal portion 46 define an interior cylindrical lumen 54 that extends from the opening 30 to the terminal portion 46. Lumen 54 has a proximal first portion 56 that has a predetermined first length which tapers inwardly from orifice 30. Lumen 54 also has a second lumen portion 58 which extends distally from the first lumen portion 56 to the terminal portion 46. Second lumen portion 58 has a predetermined length which is greater than that of the first lumen portion 56. Second lumen portion 58 has an inside diameter which is uniform throughout its length and does not taper. As is best shown in FIGS. 5 and 8, the terminal portion 46 has a lateral or horizontally extending wall portion that consists of the centrally disposed, circular base 56 of the post member 48 and four (4) radiating members 62 A-D. These define apertures 64 A-D. Radiating members 62 also define an exterior ledge 66. Preferably, the ledge 66 has a chamfered edge 68. The terminal portion 46 functions to permit distal flow of fluid to the cap member 14 as described further below, and also facilitates optimized spray formation.

The grip area or pattern 22 is disposed approximately at the midsection of the base member 12. The length of the grip area 22 is preferably 3/16 in. The proximal end 16 of the base member 12 is attachable to the distal or output end of the syringe 20 via the open or female type orifice 30. The proximal end 16 has the flange arrangement including the pair of opposing flanges 32 A and B. In the embodiment shown, the base member 12 has a preferred length of 1.015 in. The diameter of the post 48 is approximately 0.096 in, and importantly is less then a mating portion of the cap 14 describe below.

A preferred embodiment of the cap member 14 is shown in detail in FIGS. 10-14. The cap member 14 has a generally cylindrical configuration with a length that is less than that of the base member 12 and an outside diameter that is greater than that of the base or base member 12. The cap 14 has a cylindrical, longitudinal wall portion 70 with a proximal orifice 72, a radius edge portion 74, a distal recessed (bowl shaped) end portion 76, and a terminal spray discharge aperture or orifice 78. In the embodiment shown, the wall portion 70 has a preferred length of 0.380 in., and an outside diameter of 0.280 in. The recessed end bowl portion 76 has a diameter of 0.380 in. And the terminal spray orifice has a diameter of 0.012.

The wall portion 70 of cap 14 and other exterior elements define an interior cylindrical lumen 80 that extends from orifice 72 to the terminal spray orifice 78. The lumen 80 includes a proximal, cylindrical first portion 82, an inwardly tapered or conical second portion 84, a cylindrical third portion 86, a cylindrical fourth portion 88, and a distal, tapered fifth portion 90 which is communicatively connected with the discharge aperture 78. As is best shown in FIGS. 11-14, the second 84, third 86, and fourth 88 portions of the lumen 80 further have a rectilinear wall structure whereby they form opposing wall structures separated at 120 degrees. The diameter of the third portion 86 is slightly greater than that of the base post 48. A detent ring 92 is disposed at a predetermined point on the first portion 82 aligned for male to male type tandem mating with the male-type ring 52 of the base 12 to provide a firm snap type connection between the cap 14 and the base 12. The intersection of the first portion 82 and second portion 84 provides an terminal abutment 94 for connection of the base 12 to the cap 14. The third portion 86 also has a distal abutment 96. The first portion 82 (including the detent ring 92 and abutment 94) primarily functions as a structural connection between the base 12 and the cap 14. The second 84, third 86, fourth 88 and fifth 90 portions of the cap lumen 80 provide a tortuous distal flow path for fluid input from the fluid supply 20 at proximal orifice 30, transmitted through the base lumen 54, to the spray discharge aperture 78. Simultaneously, in combination with the base member 12 terminal portion 46 structure, they atomize or aerosolize the liquid to form small droplets of liquid in a predetermined spray pattern.

Figure 3:
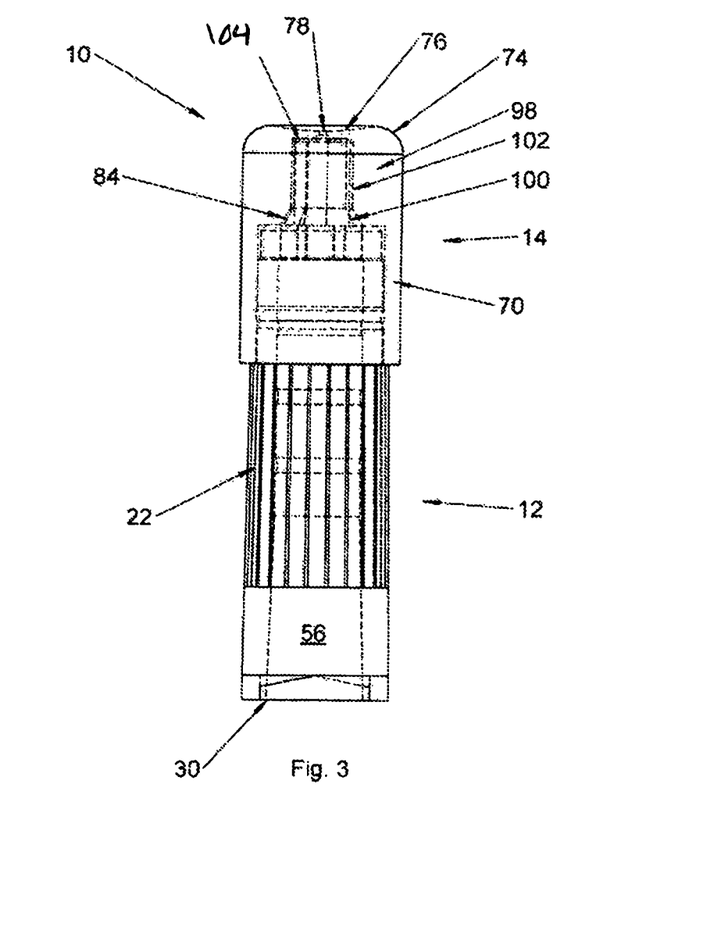
Figure 4:
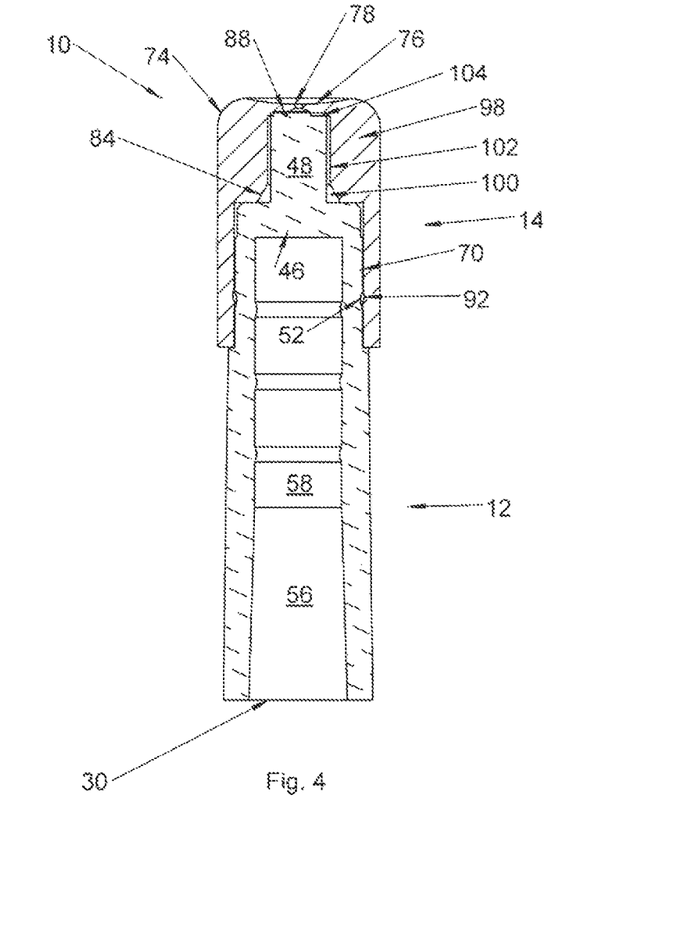

Returning to FIGS. 3 and 4, the cap 14 is connected to the base 12 via a snap type connection to form a spray device 10. The combined members 12 and 14 distally transmit fluid from the fluid source 20 and atomize the fluid for discharge at the terminal spray aperture 78 into a predetermined optimal spray pattern or profile. When operatively connected, the distal end of the base 12, at the level of the second lumen portion 58 of the base lumen 54 mates with and is fit within and covered by the first portion 82 of the cap lumen 80. And base 12 post 48 has a predetermined diameter and length less than those of the third portion 86 whereby it fits within the second 84 and third 86 portions of the cap lumen 80 yielding a fluid transmission space 98 surrounding the post 48. Transmission space 98 includes proximal conical region 100, intermediary, vertical region 102 and distal, lateral region 104 which is in fluid communication with fourth portion 88.

Figure 15:
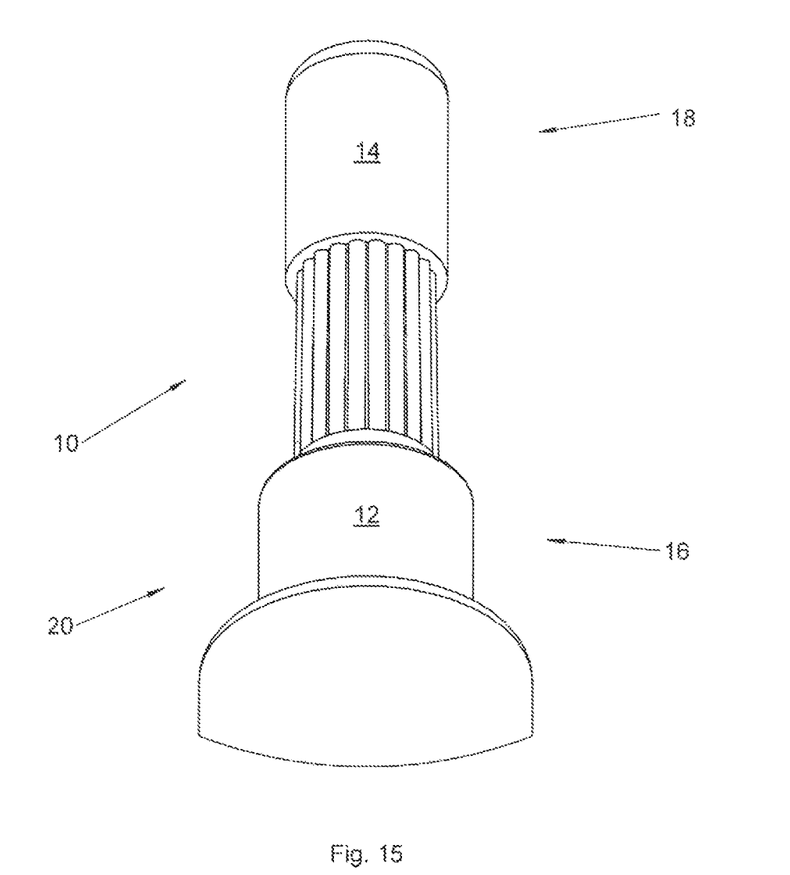

The sprayer is easily connectible and disconnectible to a fluid source such as a syringe. The radiating members 62 and apertures 64 of the base 12 are aligned with and are in fluid communication with the tapered second portion 84 of the cap 14 lumen 80. The embodiment shown and described is optimized for use with a 2 ml. syringe. However, it may be used with 1-3 ml. syringes. And, it is within the purview of the invention that the device of the invention may be scaled larger or smaller for delivering larger or smaller amounts or doses of spray fluids. The sprayer 10 may be connected directly to a syringe 20 as shown in FIG. 15. Alternatively, it may be connected to an intermediary device such as a rigid or flexible extension device.

The sprayer 10 is useful for a variety of spray applications. It is particularly useful for veterinary health and medical applications. And it is most particularly well suited for intra-nasal equine health and medical applications such as administering vaccines, medicaments or other fluid compositions.

Although the spray apparatus is described in terms of vertical, horizontal, transverse (lateral), longitudinal, and the like, it should be understood that variations from the absolute vertical, horizontal, transverse, and longitudinal are also within the scope of the present invention.

2. Equine Vaccine and Vaccination Methods of Use.

There are many diseases that target the respiratory organs or the upper respiratory tract of an animal, including human, such as bacterial infections (e.g. *Mannheimia* infection; streptococci infection, *Haemophilus* infection) or viral infections (e.g. influenza virus infection; rhinovirus infection, coronavirus infection; adenovirus infection).

Administration of a medicine or vaccine against these infection is preferably done by administration to the upper respiratory tract of the animal. Administration to the upper respiratory tract could take place via for example the mouth of the animal (oral administration of a fine mist of particles to reach the pharynx and optionally the larynx) or intranasal administration. Intranasal administration has proven to lead to a good mucosal immune response against the microorganism.

Currently the vaccine or medicine is typically administered via an applicator tip which may be attached to a syringe or other container containing the vaccine or medicine. The applicator tip is inserted in the nose of the animal to reach the upper part of the nasal cavity or the pharyngeal cavity of the animal. For animals with a long intranasal cavity such as horses and cows, the applicator tip is usually a long tube which is inserted all the way into the nasal cavity to reach the upper part of the nasal cavity where the mucal tissue is. Most animals do not like the insertion of long tube up into their noses. Animals may react violently when trying to insert such a long nasal tube and the administration of the vaccine or medicine may then be suboptimal or even impossible. The fluid sprayer of the present invention does not require a long tube to reach the upper part of the nasal cavity. It was found that the fluid sprayer of the present invention administers the fluid all the way up into the nasal cavity of an animal as good as or even better than a long tube. When using the fluid sprayer of the present invention, the animal remains very calm and accepts the fluid sprayer and the fluid administered into the nasal cavity with little or no adverse reaction.

As is well known in the art, intranasal administration is defined as administration 'by way of the nasal structures' (Merriam-Webster online dictionary (m-w.com); or as: administration 'within the nose' (The American Heritage® Medical Dictionary, Houghton Mifflin Company).

The atomization provides a mist of vaccine particles having an (volume) average particle size below 50 µm in diameter. It is recognized that by having smaller particles, a larger the surface of the mucosa that can be directly reached by the vaccine. This is believed to lead to an improved immune response. A particle size below 50 µm has proven to be practical and adequate for eliciting an immune response. In a further embodiment the average particle size is between 20 and 40 µm in diameter.

Example 1

Figure 1:
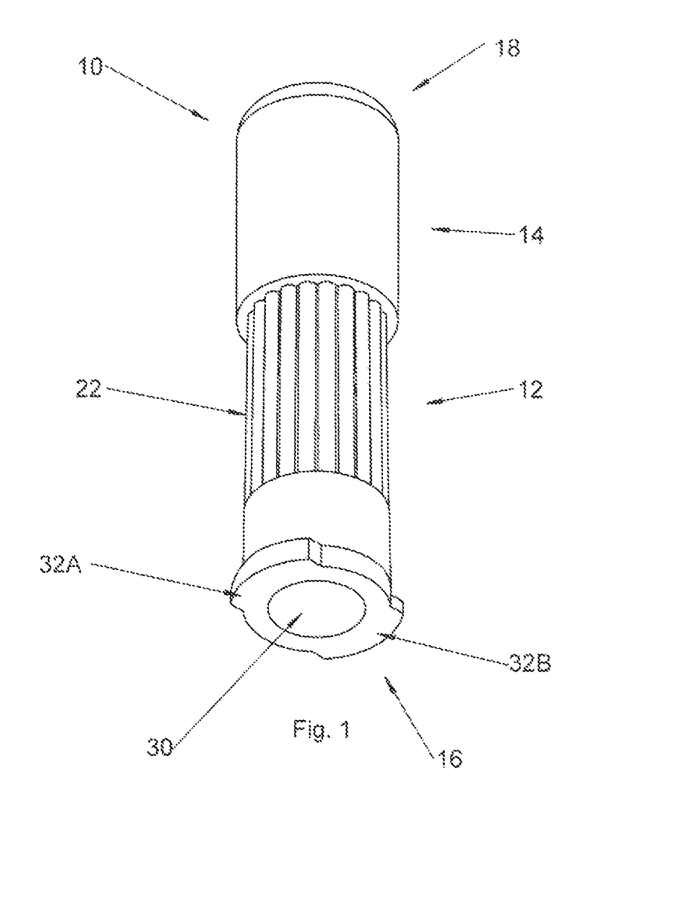
Figure 2:
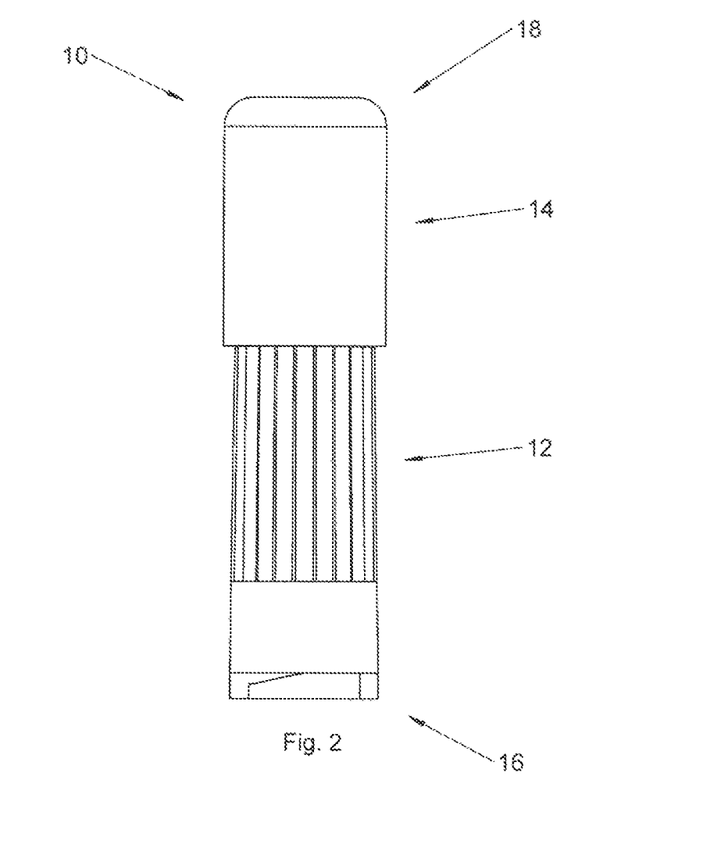

A spray test apparatus was used to simulate the effect of a cannula when applied in the nostril of a horse. A grid made up of 1 inch squares covering an 11×17 inch paper was developed to quantify the extent of the spray into the device. The grid paper is rolled into a tube, with the square grid inward, then inserted into the top of the apparatus. 1.0 mL of 0.1% blue dye solution is loaded into a syringe. The cannula to be tested is secured to the syringe via the luer lock. Syringe with cannula are inserted into the bottom of the test apparatus and contents are "administered" by pushing the syringe plunger. This coats the paper inside the device with the blue dye. The paper is removed, flattened out and the dye pattern is analyzed for coverage of the grid. Four (4) different cannulas are used:
1. A sprayer disclosed in FIG. 1 of the present invention
2. FLU AVERT cannula (available from Merck Animal Health).
3. PINNACLE Cannula (available from Zoetis)
4. CALVENZA Cannula (ex BIVI)
Results of the test are summarized in the Table 1.

TABLE 1

| Cannula | Grid Squares Covered | Length (cm). | Description |
|---|---|---|---|
| 1 | >80 | 14 | Broad dispersion of particles |
| 2 | 12 | 9 | Narrow dispersion; with some broader dispersion in the end |

TABLE 1-continued

| Cannula | Grid Squares Covered | Length (cm). | Description |
|---|---|---|---|
| 3 | 11 | 11 | Very narrow dispersion |
| 4 | 19 | 12 | Narrow dispersion with some liquid come running back |

Example 2

The four different cannulas were tested in an equine model, using a different dye for each cannula. The horse was euthanized and the head sawed in half to determine the coverage. The spray atomizer cannula of the present invention (yellow dye) demonstrated surprisingly good results in terms of equine comfort. In spite of its short length of less than 3 cm., had better and deeper coverage than a longer (greater than 15 cm) conventional cannulas (green dye). The prior art Cannulas 2-4 dispensed a "stream" of vaccine, some of which ran out of the nose of the horse following administrations. These cannulas are all long, over 15 cm., and not always readily accepted by the horse. The spray device 1 of the present invention is short, less than 3 cm. and consistently dispensed a surface covering mist which was retained in the nose of the horse. The sprayer is user friendly in addition to being horse friendly.

Vaccines may be based on either a modified live (attenuated), an inactivated pathogen or on a subunit vaccine based on one or more important immunogens derived from a pathogen. Vaccines exist for each pathogen separate, but also combination vaccines, for example for protection against Equine Influenza Virus (EIV), Equine Herpes Virus (EHV), and tetanus, exist.

It is noted that the term "vaccine" in the sense of this invention is a constitution suitable for application to an animal, comprising one or more antigens in an immunologically effective amount (i.e. capable of stimulating the immune system of the target animal sufficiently to at least reduce the negative effects of a challenge of the wild-type micro-organisms), typically combined with a pharmaceutically acceptable carrier such as a liquid containing water, optionally comprising immunostimulating agents (adjuvants), which upon administration to the animal induces an immune response for treating a disease or disorder, i.e. aiding in preventing, ameliorating or curing the disease or disorder.

In general, a vaccine may be manufactured by using art-known methods that basically comprise admixing the antigens (or a composition containing the antigens) with a pharmaceutically acceptable carrier, e.g. a liquid carrier such as (optionally buffered) water or a solid carrier such as commonly used to obtain freeze-dried vaccines. For a live vaccine an immunologically effective amount is typically between $10^4$-$10^9$ CFU/dose for bacteria and between $10^3$-$10^{10}$ TCID$_{50}$/dose for viruses, although depending on the attenuation the number may be lower (for less attenuated micro-organisms) or higher (for more attenuated micro-organisms). Optionally other substances such as adjuvants, stabilizers, viscosity modifiers or other components are added depending on the intended use or desired properties of the vaccine. For vaccination many forms are suitable, in particular liquid formulations (with dissolved, emulsified or suspended antigens; typical administration volumes are between 0.1 and 10 ml, preferably between 0.2 and 5 ml, preferably 2 ml or less) but also solid formulations such as powders for atomization devices may be suitable.

In an embodiment the vaccine comprises live attenuated infectious equine influenza virus.

In a further embodiment, the vaccine according to the invention is applied by a single administration. The administered volume may be divided over both nostrils.

The term attenuated as used herein refers to the incapability of a microorganism, in particular a bacterium or virus, of inducing a full suite of symptoms of the disease that is normally associated with its virulent (often wild-type) pathogenic counterpart. It may be attenuated such that it does not replicate within a host cell or animal, or replicate at a rate which is not significantly detrimental to the cell or animal, and/or does not induce a detrimental host response. An attenuated strain may exhibit a reduced ability to survive in a host, and may contain one or more mutations in one or more virulence genes as is commonly known in the art.

Pharmaceutical compositions comprising an active agent or compound for nasal administration are well known. The pharmaceutical composition comprise a therapeutically effective amount of the active agent or a pharmaceutically acceptable salt thereof and possibly other ingredients. The pharmaceutical compositions for nasal administration may further comprise an ingredient selected from the group comprising a permeation enhance (e.g. propylene glycol), solvents (e.g. ethanol, Cremophor, water), crystallization inhibitors (e.g. Vitamin E acetate, octyl palmitate, natural oils).

Suitable dosage formulations and methods of administering the agents can be readily determined by those of skill in the art.

To prepare the intranasal pharmaceutical compositions, one or more active agents may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see Remington's Pharmaceutical Sciences, edited by E. W. Martin (Mack Publishing Company, 18th ed., 1990). The compositions also can include stabilizers and preservatives.

Although the apparatus/method has been described in connection with the animal and human health and medical fields, it can readily be appreciated that it is not limited solely to such fields.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A fluid sprayer adapted to connect to a fluid supply, comprising
  a base member having a first end and a second end, the base member having an outer wall with an exterior surface and surrounding an interior lumen open at the first end for communicative connection to the fluid supply, the interior lumen extending to the second end, the second end having a cylindrical post member disposed outwardly from the second end, and a plurality of fluid egress apertures surrounding the post member and permitting fluid flow outwardly from the interior lumen, the post member disposed centrally within the plurality of fluid egress apertures and having a predetermined outside diameter and a predetermined length, the outside diameter of the post member being uniform along the entire length of the post member whereby the post member has a cylindrical exterior configuration, the base member outer wall further having a ledge member inset from the exterior surface of the outer wall;
  a cap member having a first end and a second end, the first end of the cap member being connected to the second end of the base member, the cap member having an outer wall with an exterior surface and surrounding an interior lumen open at the first end of the cap member and communicatively connected to the interior lumen of the base member through the plurality of fluid egress apertures, the cap member further having a spray discharge aperture disposed at the second end of the cap member, communicatively connected to the cap member interior lumen;
  wherein the cap member interior lumen has a first portion for mating with the exterior surface of the outer wall of the base member whereby the first end of the cap member abuts the ledge member of the base member, a tapered second portion fluidically communicatively connected to the base member at the plurality of fluid egress apertures of the base member, a cylindrical third portion extending from the tapered second portion, and a cylindrical fourth portion extending from the cylindrical third portion to the spray discharge aperture, the cylindrical fourth portion having a diameter less than that of the cylindrical third portion;
  wherein the tapered second portion, the cylindrical third portion and the cylindrical fourth portion are each formed of a plurality of rectilinear walls; and
  wherein the entire post member of the base member is disposed in a space defined by the tapered second portion and the cylindrical third portion of the cap member interior lumen, the diameter of the post member of the base member being less than the diameter of the cylindrical third portion of the cap member lumen and the length of the post member being equal to a combined length of the tapered second and cylindrical third portions of the cap member interior lumen, whereby the fluid flowing outwardly from the plurality of fluid egress apertures enters a tortuous distal fluid flow path formed between the post member and the rectilinear walls of the tapered second, cylindrical third, and cylindrical fourth portions of the cap member interior lumen, which aerosolizes fluid discharged from the spray discharge aperture.

2. The fluid sprayer of claim 1, wherein the fluid sprayer consists of the base member and the cap member, the base and cap members being connected during spraying via a snap-type connection, the base and cap members having complementary, aligned male and female type detents.

3. The fluid sprayer of claim 1 wherein the base member has a tubular, cylindrical and elongated configuration.

4. The fluid sprayer of claim 3, wherein
the base member interior lumen has a tapered first portion extending from the first end of the base member, and a cylindrical second portion extending from the first portion to the plurality of fluid egress apertures,
wherein the cylindrical second portion has a diameter less than a diameter of the tapered first portion, whereby the change from tapered to cylindrical geometry and the reduction in diameter along the interior lumen of the base member reduces a residual volume of fluid flow throughput from the fluid supply connected at the first end of the base member towards the plurality of fluid egress apertures; and
wherein the plurality of fluid egress apertures comprises four spaced apart fluid egress apertures, the four fluid egress apertures having a segmental geometry and being separated from each other by radial members.

5. The fluid sprayer of claim 3, wherein the cap member has a short, tubular, cylindrical configuration with a predetermined length, wherein the base member has a predetermined length, and wherein the length of the cap member is less than one half the length of the base member.

6. The fluid sprayer of claim 1, wherein the base member has grip means disposed on the exterior surface of the base member.

7. The fluid sprayer of claim 1, wherein the cylindrical fourth portion rectilinear walls are separated at 120 degrees.

8. The fluid sprayer of claim 1, further comprising a terminal tapered, fifth portion of the cap member interior lumen extending from the cylindrical fourth portion to the spray discharge aperture, the tapered fifth portion having a diameter less than a diameter of the cylindrical fourth portion.

9. The fluid sprayer of claim 1, further comprising an inwardly tapered region on the second end of the cap member surrounding the spray discharge aperture.

10. A method to protect an animal against an infection caused by a microorganism comprising administering, by intranasal atomization, a vaccine comprising an antigen to upper respiratory tract of the animal by using the fluid sprayer of claim 1.

11. The method according to claim 10 wherein the antigen is a live, attenuated or killed microorganism or an immunogenic fragment thereof.

12. The method according to claim 10 wherein the antigen is selected from the group consisting of bacterium, virus, and protozoan.

13. The method according to claim 10 wherein the antigen is a life influenza virus.

14. The method according to claim 10 wherein the animal is selected from the group consisting of equine, ruminant, feline, canine.

15. The method according to claim 10 wherein the animal is equine or ruminant.

16. The method according to claim 10 wherein the microorganism is an equine microorganism.

17. A method of treating an infection in an animal caused by a microorganism comprising administering, by intranasal atomization, a liquid composition comprising a compound effective in treatment of the infection to an upper respiratory tract of the animal by using the fluid sprayer of claim 1.

18. The method according to claim 17 wherein the compound is selected from the group consisting of bacterium, virus, and protozoan.

19. The method according to claim 17 wherein the animal is selected from the group consisting of equine, ruminant, feline, canine.

20. The method according to claim 19 wherein the animal is equine or ruminant.

21. The method according to claim 17 wherein the microorganism is an equine microorganism.

22. A fluid sprayer adapted to connect to a fluid supply, the fluid sprayer having a proximal, first end for connection to the fluid supply and a distal, second end from which fluid is sprayed, comprising:
a tubular, cylindrical and elongated base member having a proximal first end and a distal second end, the base member having an outer wall with an exterior surface and surrounding an interior lumen open at the first end for communicative connection to the fluid supply, the interior lumen extending to the second end of the base member, the second end of the base member having four fluid egress apertures separated by radial members, the interior lumen of the base member having a tapered first portion extending from the open first end of the base member, and a cylindrical second portion extending from the first portion to the fluid egress apertures, the base member further having a cylindrical post member disposed centrally within the fluid egress apertures and disposed outwardly from the second end of the base member, the fluid egress apertures surrounding the post member and permitting fluid flow outwardly from the interior lumen, the post member having a predetermined outside diameter and a predetermined length, the outside diameter of the post member being uniform along the entire length of the post member whereby the post member has a cylindrical exterior configuration, the base member outer wall further having a ledge member inset from the exterior surface of the outer wall; and
a short tubular, cylindrical cap member having a proximal, first end and a distal second end, the first end of the cap member being connected, during spraying, to the second end of the base member, the cap member having an outer wall with an exterior surface and surrounding an interior lumen open at the first end of the cap member and communicatively connected to the interior lumen of the base member through the fluid egress apertures, the cap member further having an open spray discharge aperture disposed at the second end of the cap member, fluidically communicatively connected to the cap member interior lumen, the fluid egress apertures, and the interior lumen of the base member, the cap member interior lumen further having:

a first portion for mating with the exterior surface of the outer wall of the base member whereby the first end of the cap member abuts the ledge member of the base member;

a tapered second portion fluidically communicatively connected to the fluid egress apertures of the base member, a cylindrical third portion extending from the tapered second portion, a cylindrical fourth portion extending from the cylindrical third portion, the cylindrical fourth portion having a diameter less than that of the cylindrical third portion;

wherein the tapered second portion, the cylindrical third portion and the cylindrical fourth portions are each formed of a plurality of rectilinear walls;

wherein the cylindrical fourth portion rectilinear walls are separated at 120 degrees;

further comprising a terminal tapered, fifth portion extending from the cylindrical fourth portion to the spray discharge aperture; and wherein the entire post member of the base member is disposed in a space defined by the tapered second portion and the cylindrical third portion of the cap member interior lumen, the diameter of the post member of the base member being less than the diameter of the cylindrical third portion of the cap member lumen and the length of the post member being equal to a combined length of the tapered second and cylindrical third portions of the cap member interior lumen, whereby fluid flowing outwardly from the fluid egress apertures enters a tortuous distal fluid flow path formed between the post member and the rectilinear walls of the tapered second, cylindrical third, and cylindrical fourth portions of the cap member interior lumen, which aerosolizes fluid discharged from the spray discharge aperture.

23. A liquid sprayer adapted to connect to a fluid supply syringe for delivering medicaments and vaccines to animals and humans, the liquid sprayer having a proximal, first end for connection to the fluid supply and a distal, second end from which fluid is sprayed, comprising:

A. a tubular, cylindrical and elongated base member having a proximal first end and a distal second end, the base member having:

an outer wall with an exterior surface and surrounding an interior lumen open at the first end of the base member for communicative connection to the fluid supply syringe, the interior lumen extending to the second end of the base member, the second end of the base member having a plurality of fluid egress apertures separated by at least one radial member, the interior lumen of the base member having a tapered first portion extending from the first end of the base member, and a cylindrical second portion extending from the first portion to the plurality of fluid egress apertures, the base member further having a cylindrical post member disposed centrally within the plurality of fluid egress apertures and at the second end of the base member extending outwardly, the post member having a predetermined length and a predetermined outside diameter, the outside diameter being uniform throughout the entire length of the post member whereby the post member has a cylindrical exterior configuration, the base member outer wall further having a ledge member inset from the exterior surface of the outer wall, the fluid egress apertures surrounding the post member and permitting fluid flow outwardly from the interior lumen, the cylindrical second portion further having a diameter less than a diameter of the tapered first portion, whereby the change from tapered to cylindrical geometry and the reduction in diameter along the interior lumen of the base member reduces a residual volume of fluid flow throughput from the fluid supply connected at the first end of the base member towards the plurality of fluid egress apertures; and B. a short, tubular, cylindrical cap member having a proximal first end and a distal second end, the cap member having a length less than one half a length of the base member, the first end of the cap member being fixedly connected, during spraying, to the second end of the base member, the cap member having an outer wall with an exterior surface and surrounding an interior lumen open at the first end of the cap member and communicatively connected to the interior lumen of the base member through the plurality of fluid egress apertures, the cap member further having an open spray discharge aperture disposed at the second end of the cap member, the spray discharge aperture being fluidically communicatively connected to the interior cap member lumen, the plurality of fluid egress apertures, and the base member lumen, the interior cap member lumen further having:

i. a first portion for mating with the exterior surface of the outer wall of the base member, whereby the first end of the cap member abuts the ledge member of the base member, ii. a tapered second portion fluidically communicatively connected to the plurality of fluid egress apertures of the base member, and iii. a cylindrical third portion extending from the tapered second portion of the cap member to the spray discharge aperture, iv. a cylindrical fourth portion extending from the third portion of the cap member, the fourth portion having a diameter less than that of the third portion of the cap member; and v. a terminal tapered, fifth portion extending from the cylindrical fourth portion of the cap member to the spray discharge aperture, the fifth portion having a diameter less than a diameter of the fourth portion;

the entire cap member remaining connected to the base member during use;

wherein the tapered second portion of the cap member, the cylindrical third portion of the cap member, and the cylindrical fourth portion of the cap member are each formed of a plurality of rectilinear walls;

wherein the cylindrical fourth portion rectilinear walls are separated at 120 degrees;

wherein the cap member further comprises an inwardly tapered region disposed on an exterior of the second end of the cap member surrounding the spry discharge aperture;

C. wherein the entire post member of the base member is disposed in a space defined by the tapered second portion and cylindrical third portion of the interior cap member lumen, the diameter of the post member of the base member being less than the diameter of the cylindrical third portion of the cap member lumen and the length of the post member being equal to a combined length of the tapered second and cylindrical third portions of the cap member lumen, whereby fluid flowing outwardly from the fluid egress apertures enters a tortuous distal fluid flow path formed between the post member and the rectilinear walls of the tapered second, cylindrical third, and cylindrical fourth portions of the interior cap member lumen, which aerosolizes fluid discharged from the spray discharge aperture; and D. wherein the base member has a luer lock fitting for connection to the fluid supply syringe.

\* \* \* \* \*